US00PP35471P2

(12) United States Plant Patent
de Vos

(10) Patent No.: US PP35,471 P2
(45) Date of Patent: Nov. 14, 2023

(54) ***HYDRANGEA* PLANT NAMED 'HORE1602'**

(50) Latin Name: *Hydrangea macrophylla*
Varietal Denomination: HORE1602

(71) Applicant: KWEKERIJ LENDERT de VOS B.V., Reeuwijk (NL)

(72) Inventor: Lendert de Vos, Reeuwijk (NL)

(73) Assignee: KWEKERIJ LENDERT de VOS B.V., Reeuwijk (NL)

( * ) Notice: Subject to any disclaimer, the term of this patent is extended or adjusted under 35 U.S.C. 154(b) by 0 days.

(21) Appl. No.: 18/103,123

(22) Filed: Jan. 30, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Karen M Redden
(74) *Attorney, Agent, or Firm* — C. Anne Whealy

(57) ABSTRACT

A new and distinct cultivar of *Hydrangea* plant named 'HORE1602', characterized by its relatively compact, upright to broadly spreading plant habit; moderately vigorous growth habit; freely branching habit; strong and sturdy stems; dark green-colored leaves; freely flowering habit; large mophead inflorescences that are initially yellowish green in color with pink sectors developing proximally; and good postproduction longevity and garden performance.

2 Drawing Sheets

Figure 1:
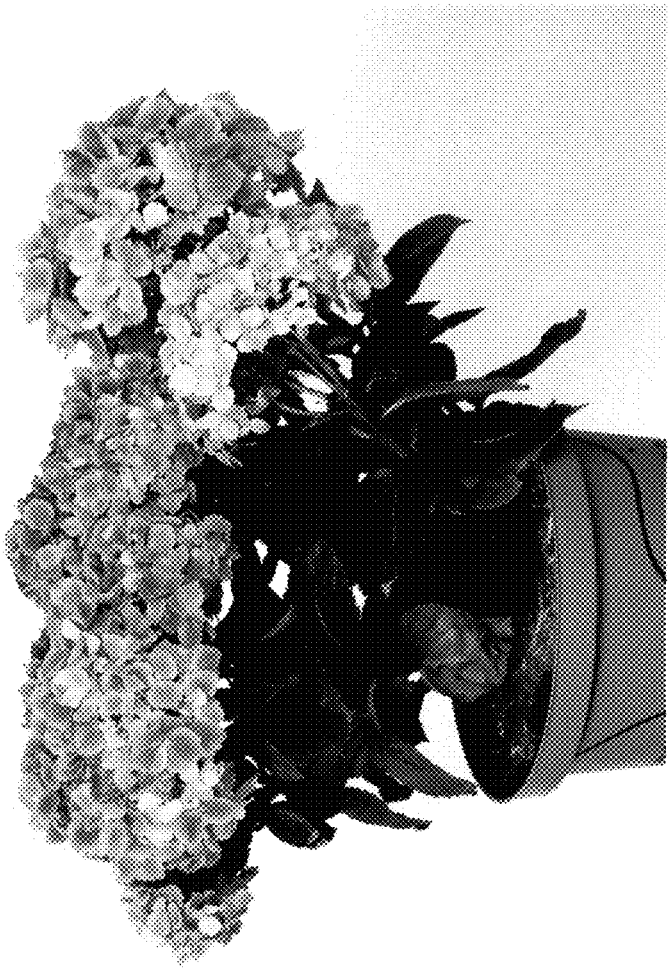

Botanical designation: *Hydrangea macrophylla.*
Cultivar denomination: 'HORE1602'.

BACKGROUND OF THE INVENTION

The present invention relates to a new and distinct cultivar of *Hydrangea* plant, botanically known as *Hydrangea macrophylla*, commercially referred to as a Mophead *Hydrangea*, and hereinafter referred to by the name 'HORE1602'.

The new *Hydrangea* plant is a product of a planned breeding program conducted by the Inventor in Reeuwijk, The Netherlands. The objective of the breeding program is to create new compact, strong and sturdy *Hydrangea* plants with attractive inflorescences and good postproduction longevity.

The new *Hydrangea* plant originated from a cross-pollination conducted by the Inventor during the summer of 2014 of a proprietary selection of *Hydrangea macrophylla* identified as code number 13-10031-01, not patented, as the female, or seed, parent with a proprietary selection of *Hydrangea macrophylla* identified as code number 12-00-09, not patented, as the male, or pollen, parent. The new *Hydrangea* plant was discovered and selected as a single flowering plant from within the progeny of the stated cross-pollination in a controlled greenhouse environment in Reeuwijk, The Netherlands in August, 2016.

Asexual reproduction of the new *Hydrangea* plant by terminal vegetative cuttings since August, 2018 in a controlled greenhouse environment in Reeuwijk, The Netherlands has shown that the unique features of this new *Hydrangea* plant are stable and reproduced true to type in successive generations of asexual reproduction.

SUMMARY OF THE NEW PLANT

Plants of the new *Hydrangea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HORE1602'. These characteristics in combination distinguish 'HORE1602' as a new and distinct *Hydrangea* plant:

1. Relatively compact, upright to broadly spreading plant habit.
2. Moderately vigorous growth habit.
3. Freely branching habit.
4. Strong and sturdy stems.
5. Dark green-colored leaves.
6. Freely flowering habit.
7. Large mophead inflorescences that are initially yellowish green in color with pink sectors developing proximally.
8. Good postproduction longevity and garden performance.

Plants of the new *Hydrangea* can be compared to plants of the female parent selection. Plants of the new *Hydrangea* differ primarily from plants of the female parent selection in the following characteristics:

1. Leaves of plants of the new *Hydrangea* are lighter green in color than leaves of plants of the female parent selection.
2. Sterile flowers of plants of the new *Hydrangea* are initially yellowish green in color with pink sectors developing proximally whereas sterile flowers of plants of the female parent selection are light pink in color.

Plants of the new *Hydrangea* can be compared to plants of the male parent selection. Plants of the new *Hydrangea* differ primarily from plants of the male parent selection in the following characteristics:

1. Leaves of plants of the new *Hydrangea* are darker green in color than leaves of plants of the male parent selection.
2. Sterile flowers of plants of the new *Hydrangea* are initially yellowish green in color with pink sectors developing proximally whereas sterile flowers of plants of the male parent selection are pink in color.

Plants of the new *Hydrangea* can be compared to plants of *Hydrangea macrophylla* 'HBA215910', disclosed in U.S. Plant Pat. No. 29,171. In side-by-side comparisons, plants of the new *Hydrangea* differ primarily from plants of 'HBA215910' in the following characteristics:

1. Inflorescences of plants of the new *Hydrangea* are firmer and denser than inflorescences of plants of 'HBA215910'.
2. Sterile flowers of plants of the new *Hydrangea* are initially yellowish green in color with pink sectors developing proximally whereas sterile flowers of plants of 'HBA215910' are dark red purple in color with green-colored sectors.
3. Plants of the new *Hydrangea* have longer postproduction longevity and better garden performance than plants of 'HBA215910'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HORE1602' grown in a container.

Figure 2:
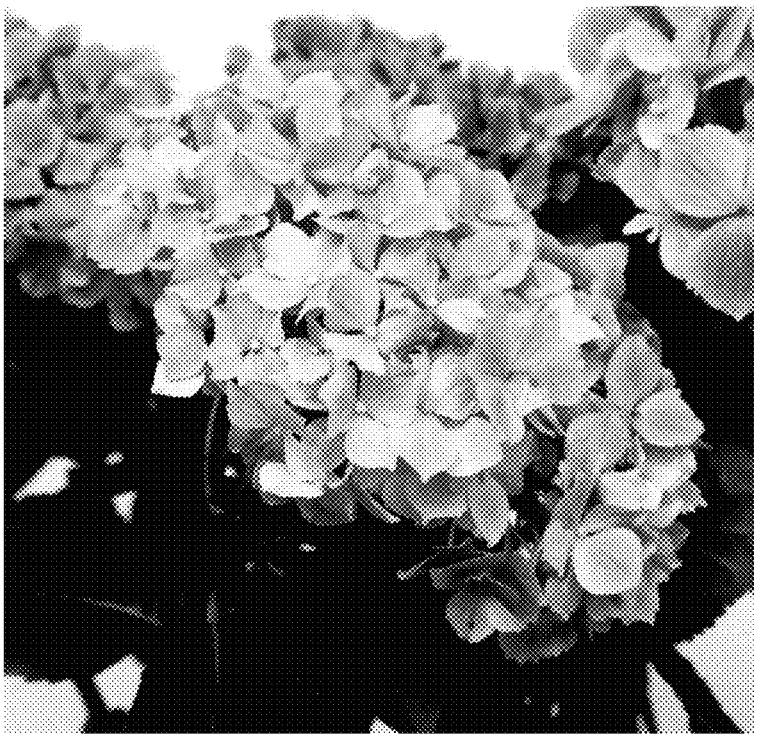

The photograph at the top of the second sheet (FIG. 2) is a close-up view of typical inflorescences of 'HORE1602'.

Figure 3:
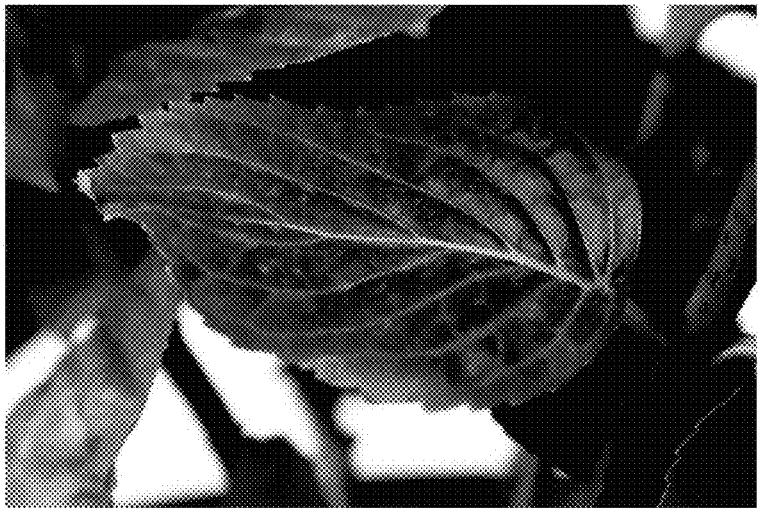

The photograph at the bottom of the second sheet (FIG. 3) is a close-up view of a typical leaf of 'HORE1602'.

DETAILED BOTANICAL DESCRIPTION

Plants used in the aforementioned photographs and in the following description were grown during the summer in ground beds and 19-cm containers in an outdoor nursery in Reeuwijk, The Netherlands and under cultural practices typical of commercial *Hydrangea* production. During the production of the plants, day temperatures ranged from 18° C. to 32° C., night temperatures ranged from 8° C. to 20° C. Plants of the new *Hydrangea* were pinched in the early summer. Plants were 18 months old when the photographs and description were taken. In the following description, color references are made to The Royal Horticultural Society Colour Chart, 2015 Edition, except where general terms of ordinary dictionary significance are used. Mophead *Hydrangea* plants with yellowish green-colored sterile flowers are not typically treated with aluminum sulfate to "blue" the flower color.

Botanical description: *Hydrangea macrophylla* 'HORE1602'.

Parentage:

*Female, or seed, patent*.—Proprietary selection of *Hydrangea macrophylla* identified as code number 13-10031-01, not patented.

*Male, or pollen, patent*.—Proprietary selection of *Hydrangea macrophylla* identified as code number 12-00-09, not patented.

Propagation:

*Type cutting*.—By vegetative terminal cuttings.

*Time to initiate roots, summer*.—About 16 days at temperatures ranging from 20° C. to 30° C.

*Time to produce a rooted young plant, summer*.—About four months at temperatures ranging from 20° C. to 30° C.

*Root description*.—Medium in thickness; fibrous; typically light brown in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Relatively compact, upright to broadly outwardly spreading and mounding plant habit; flattened globular in overall shape; strong and sturdy stems; moderately vigorous growth habit and moderate growth rate; about six months from planting rooted young plants are required to produce small finished plants.

*Plant height*.—About 30.4 cm.

*Plant diameter or area of spread*.—About 47.2 cm.

Lateral branch description:

*Branching habit*.—Freely branching habit with about seven lateral branches developing per plant; pinching is not required, but will enhance lateral branch development.

*Length*.—About 18.5 cm.

*Diameter*.—About 8 mm.

*Internode length*.—About 3.4 cm.

*Strength*.—Strong, sturdy.

*Aspect*.—About 60° from vertical.

*Texture*.—Smooth, glabrous; becoming woody with subsequent development.

*Color, developing*.—Close to 145B.

*Color, fully developed*.—Close to 146B and at the internodes, strongly tinged with close to a blend of N186A and 202A; when woody, close to 199A to 199C.

*Lenticels*.—Density: Sparse to medium density. Length: About 1.75 mm. Diameter: About 0.75 mm. Color: Close to N186B.

Leaf description:

*Arrangement*.—Opposite, simple.

*Length*.—About 9 cm.

*Width*.—About 7.9 cm.

*Shape*.—Cordate to broadly ovate.

*Apex*.—Broadly apiculate.

*Base*.—Cordate to truncate.

*Margin*.—Coarsely dentate to serrate.

*Texture, upper and lower surfaces*.—Slightly rugose, glabrous.

*Venation pattern*.—Pinnate.

*Color*.—Developing leaves, upper surface: Close to NN137A. Developing leaves, lower surface: Close to 137B. Fully developed leaves, upper surface: Close to a blend of NN137B and 139A; venation, close to 146A to 146B. Fully developed leaves, lower surface: Close to 147B; venation, close to 146B.

*Petioles*.—Length: About 1.4 cm. Diameter: About 3 mm by 5 mm. Texture and luster, upper surface: Smooth, glabrous; slightly glossy. Texture and luster, lower surface: Smooth, glabrous; moderately glossy. Color, upper surface: Close to 144B; towards the margins, close to 146B. Color, lower surface: Close to 144A; proximally, close to 146A.

Flower description:

*Flower type and habit*.—Showy rotate sterile flowers that are slightly to cup-shaped and small, inconspicuous rotate fertile flowers arranged on terminal panicles; panicles mophead and flattened globular in overall shape; panicles firm and dense; sterile flowers face upright, outwardly to slightly drooping and fertile flowers face mostly upright; fertile flowers do not develop past the bud stage.

*Fragrance*.—No fragrance detected.

*Natural flowering season*.—In the garden, plants flower continuously from the late spring to late summer in The Netherlands.

*Flower longevity*.—Good postproduction longevity; sterile flowers maintain good substance for about six weeks on the plant, sterile flowers persistent; fertile flowers typically do not develop past the bud stage.

*Quantity of flowers*.—Freely flowering habit; about 325 sterile flowers and about 125 fertile flowers per panicle.

*Panicle height*.—About 12.6 cm.

*Panicle diameter*.—About 18.8 cm.

*Panicle peduncles*.—Length: About 5.9 cm. Diameter: About 3.5 mm. Strength: Strong. Aspect: Primary peduncles, mostly erect; lateral peduncles, about 35° from primary peduncle axis. Texture and luster: Smooth, glabrous; slightly glossy. Color: Close to 144A; at the internodes, tinged with close to a blend of N186A and 202A.

*Sterile flower buds*.—Length: About 7 mm. Diameter: About 1.9 cm. Shape: Irregularly and broadly cup-shaped. Color: Close to 145A to 145B; proximally, close to 62B.

*Fertile flower buds*.—Length: About 2 mm. Diameter: About 3 mm. Shape: Broadly obovate, flattened. Color: Immature corolla, close to 151A, and immature calyx, close to 143B.

*Sterile flower diameter*.—About 3 cm to 4.9 cm.

*Sterile flower depth* (*height*).—About 5 mm to 18 mm.

*Fertile flowers*.—Fertile flowers do not develop past the bud stage.

*Petals, sterile flowers*.—Petals do not develop and abscise after the bud stage.

*Sepals, sterile flowers*.—Quantity and arrangement: Typically three or four, or occasionally five, arranged in a single whorl. Length: About 2.3 cm. Width: About 2.5 cm. Shape: Reniform to broadly obovate; flat to moderately concave or convex; sepals touching to slightly imbricate. Apex: Bluntly acute. Base: Cuneate. Margin: Coarsely dentate to crenate; slightly undulate. Texture and luster, upper and lower surfaces: Smooth, glabrous; matte. Color: When opening, upper surface: Close to 144B; towards the base, close to 63C; venation, close to 65B and 65C. When opening, lower surface: Close to 146D to lighter than 146D; towards the base, close to 62A; venation, close to 65D. Fully opened, upper surface: Close to 144A; towards the base, close to 63C; venation, close to 65B and 65C with areas adjacent to venation, close to 60D; with subsequent development, color becoming closer to 143B, towards the margins and apex, tinged with close to 180B and venation, close to 145A. Fully opened, lower surface: Close to 148C; towards the base, close to 62B; venation, close to 63C to 63D; color becoming closer to a blend of 145A and 146D with subsequent development.

*Pedicels, sterile flowers*.—Length: About 2.8 cm. Diameter: About 1.25 mm. Strength: Moderately strong. Aspect: About 35° from main peduncle axis. Texture and luster: Smooth, glabrous; matte. Color: Close to 65A; proximally, close to 151A.

*Pedicels, fertile flowers*.—Length: About 4 mm. Diameter: About 1 mm. Strength: Moderately strong. Aspect: About 20° from vertical. Texture and luster: Smooth, glabrous; slightly glossy. Color: Close to 151D.

*Reproductive organs, sterile flowers*.—Stamen and pistil development has not been observed on plants of the new *Hydrangea*.

*Seeds*.—To date, seed development has not been observed on plants of the new *Hydrangea*.

Pathogen & pest resistance: Plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HORE1602' as illustrated and described.

* * * * *